United States Patent
Yachi et al.

(10) Patent No.: US 10,493,148 B2
(45) Date of Patent: Dec. 3, 2019

(54) PD-1 AGONIST ANTIBODIES AND USES THEREOF

(71) Applicant: Eli Lilly and Company, Indianapolis, IN (US)

(72) Inventors: Pia Pauliina Yachi, San Diego, CA (US); Qing Chai, San Diego, CA (US); Yiqing Feng, Carmel, IN (US); Kristin Paige Newburn, Indianapolis, IN (US); Stephanie Marie Truhlar, Carlsbad, CA (US); Petra Verdino, La Jolla, CA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 16/282,609

(22) Filed: Feb. 22, 2019

(65) Prior Publication Data

US 2019/0270818 A1    Sep. 5, 2019

Related U.S. Application Data

(60) Provisional application No. 62/637,643, filed on Mar. 2, 2018.

(51) Int. Cl.
| | |
|---|---|
| *C07K 16/28* | (2006.01) |
| *A61K 39/395* | (2006.01) |
| *A61K 39/00* | (2006.01) |
| *A61P 37/06* | (2006.01) |

(52) U.S. Cl.
CPC ............ *A61K 39/395* (2013.01); *A61K 39/00* (2013.01); *A61K 39/39558* (2013.01); *C07K 16/28* (2013.01)

(58) Field of Classification Search
None
See application file for complete search history.

(56) References Cited

U.S. PATENT DOCUMENTS

| | | |
|---|---|---|
| 8,993,731 B2 | 3/2015 | Tyson |
| 9,701,749 B2 | 7/2017 | Shibayama et al. |
| 9,982,052 B2 | 5/2018 | Pantaleo et al. |
| 9,982,053 B2 | 5/2018 | Pantaleo et al. |
| 2012/0269806 A1 | 10/2012 | Sykes |
| 2014/0302070 A1 | 10/2014 | Chen et al. |
| 2017/0088618 A1 | 3/2017 | Bennett et al. |
| 2017/0166642 A1 | 6/2017 | Pantaleo et al. |
| 2017/0247454 A1 | 8/2017 | Benz et al. |
| 2018/0127502 A1 | 5/2018 | Brentjens et al. |
| 2018/0355061 A1 | 12/2018 | Chen et al. |

FOREIGN PATENT DOCUMENTS

| | | |
|---|---|---|
| EP | 2742953 A1 | 6/2014 |
| WO | 2004056875 A1 | 7/2004 |
| WO | 2006121168 A1 | 11/2006 |
| WO | 2010029434 A1 | 3/2010 |
| WO | 2010029435 A1 | 3/2010 |
| WO | 2010089411 A2 | 8/2010 |
| WO | 2011100841 A1 | 8/2011 |
| WO | 2011/110621 A1 | 9/2011 |
| WO | 2016/020856 A2 | 2/2016 |
| WO | 2017055547 A1 | 4/2017 |
| WO | 2017096026 A1 | 6/2017 |

OTHER PUBLICATIONS

Billur Akkaya et al: "Modulation of the pd-1 pathway by inhibitory antibody superagonists", Jan. 1, 2012 (Jan. 1, 2012).
Wang Liqing et al: "Programmed cell death 1 (Pd-1) and its ligand Pd—Li are required for allograft tolerance", European Journal of Immunology, Wiley VCH, Weinheim, vol. 37, No. 10, Oct. 1, 2007.
Isakov, N., *J. Autoimmune Disorders 2016*; 2(2):17.
Chothia et al., "Canonical structures for the hypervariable regions of immunoglobulins", Journal of Molecular Biology, 196, 901-917 (1987.
Al-Lazikani et al., "Standard conformations for the canonical structures of immunoglobulins", Journal of 5 Molecular Biology, 273, 927-948 (1997).
North et al., "A New Clustering of Antibody CDR Loop Conformations", Journal of Molecular Biology, 406, 228-256 (2011).
Kabat, et al., Ann. NY Acad. Sci. 190:382-93 (1971).
Weiner LJ, Fully Human Therapeutic Monoclonal Antibodies J. Immunother. 2006; 29: 1-9.
Lloyd, S., et al. (2010) The effectiveness of anti-TNFα therapies when used sequentially in rheumatoid arthritis patients: a systematic review and meta-analysis. Rheumatology, 49:2313-21).
Yanxia Guo, et al, "Immune Checkpoint inhibitor Pd-1 pathway is down-regulated in synovium at various stages of rheumatoid arthritis disease progression" PLoS One 13(2): e0192704.
Mallbris L, et al., *J. Clin. Aesthet. Dermatol.* 2016; 9: 13-15).

*Primary Examiner* — Nora M Rooney
(74) *Attorney, Agent, or Firm* — Robert L Sharp

(57) ABSTRACT

The present invention relates to anti-human PD-1 agonist antibodies, and uses thereof for treating autoimmune disorders such as rheumatoid arthritis or for decreasing rejection of transplanted cells and/or tissues.

12 Claims, No Drawings
Specification includes a Sequence Listing.

SEQUENCE LISTING

<160> NUMBER OF SEQ ID NOS: 19

<210> SEQ ID NO 1
<211> LENGTH: 449
<212> TYPE: PRT
<213> ORGANISM: Artificial Sequence
<220> FEATURE:
<223> OTHER INFORMATION: Synthetic Construct

<400> SEQUENCE: 1

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Ser Leu Ser Lys Tyr
            20                  25                  30

Asp Met Ser Trp Val Arg Gln Ala Pro Gly Lys Gly Leu Glu Trp Met
        35                  40                  45

Gly Ile Ile Tyr Thr Ser Gly Tyr Thr Asp Tyr Ala Gln Lys Phe Gln
    50                  55                  60

Gly Arg Val Thr Met Thr Glu Asp Thr Ser Thr Asp Thr Ala Tyr Met
65                  70                  75                  80

Glu Leu Ser Ser Leu Arg Ser Glu Asp Thr Ala Val Tyr Tyr Cys Ala
                85                  90                  95

Thr Gly Asn Pro Tyr Tyr Thr Asn Gly Phe Asn Ser Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140
```

```
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
        260                 265                 270

Pro Glu Val Lys Phe Asn Trp Tyr Val Asp Gly Val Glu Val His Asn
    275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 2
<211> LENGTH: 217
<212> TYPE: PRT
<213> ORGANISM: Artificial Sequence
<220> FEATURE:
<223> OTHER INFORMATION: Synthetic Construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Pro Asn Asn Leu
            20                  25                  30
```

Leu Ala Trp Tyr Gln Gln Lys Pro Gly Lys Ala Pro Lys Leu Leu Ile
            35                  40                  45

Tyr Gly Ala Ser Asp Leu Pro Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Asn Tyr Val Gly Pro
                85                  90                  95

Val Ser Tyr Ala Phe Gly Gly Thr Lys Val Glu Ile Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215

<210> SEQ ID NO 3
<211> LENGTH: 119
<212> TYPE: PRT
<213> ORGANISM: Artificial Sequence
<220> FEATURE:
<223> OTHER INFORMATION: Synthetic Construct

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Val Ser Gly Tyr Ser Leu Ser Lys Tyr
            20                  25                  30

Asp Met Ser Trp Val Arg Gln Ala Pro Gly Lys Gly Leu Glu Trp Met
        35                  40                  45

Gly Ile Ile Tyr Thr Ser Gly Tyr Thr Asp Tyr Ala Gln Lys Phe Gln
    50                  55                  60

Gly Arg Val Thr Met Thr Glu Asp Thr Ser Thr Asp Thr Ala Tyr Met
65                  70                  75                  80

Glu Leu Ser Ser Leu Arg Ser Glu Asp Thr Ala Val Tyr Tyr Cys Ala
                85                  90                  95

Thr Gly Asn Pro Tyr Tyr Thr Asn Gly Phe Asn Ser Trp Gly Gln Gly
            100                 105                 110

Thr Leu Val Thr Val Ser Ser
        115

<210> SEQ ID NO 4
<211> LENGTH: 110
<212> TYPE: PRT
<213> ORGANISM: Artificial Sequence
<220> FEATURE:
<223> OTHER INFORMATION: Synthetic Construct

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Pro Asn Asn Leu
            20                  25                  30

Leu Ala Trp Tyr Gln Gln Lys Pro Gly Lys Ala Pro Lys Leu Leu Ile
        35                  40                  45

Tyr Gly Ala Ser Asp Leu Pro Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Asn Asn Tyr Tyr Val Gly Pro
                85                  90                  95

Val Ser Tyr Ala Phe Gly Gly Gly Thr Lys Val Glu Ile Lys
            100                 105                 110

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Lys Val Ser Gly Tyr Ser Leu Ser Lys Tyr Asp Met Ser
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6

Ile Ile Tyr Thr Ser Gly Tyr Thr Asp Tyr Ala Gln Lys Phe Gln Gly
1               5                   10                  15

<210> SEQ ID NO 7
<211> LENGTH: 13
<212> TYPE: PRT
<213> ORGANISM: Artificial Sequence
<220> FEATURE:
<223> OTHER INFORMATION: Synthetic Construct

<400> SEQUENCE: 7

Ala Thr Gly Asn Pro Tyr Tyr Thr Asn Gly Phe Asn Ser
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Gln Ala Ser Gln Ser Pro Asn Asn Leu Leu Ala
1               5                   10

```
<210> SEQ ID NO 9
<211> LENGTH: 8
<212> TYPE: PRT
<213> ORGANISM: Artificial Sequence
<220> FEATURE:
<223> OTHER INFORMATION: Synthetic Construct

<400> SEQUENCE: 9

Tyr Gly Ala Ser Asp Leu Pro Ser
1               5

<210> SEQ ID NO 10
<211> LENGTH: 12
<212> TYPE: PRT
<213> ORGANISM: Artificial Sequence
<220> FEATURE:
<223> OTHER INFORMATION: Synthetic Construct

<400> SEQUENCE: 10

Gln Asn Asn Tyr Tyr Val Gly Pro Val Ser Tyr Ala
1               5                   10

<210> SEQ ID NO 11
<211> LENGTH: 1347
<212> TYPE: DNA
<213> ORGANISM: Artificial Sequence
<220> FEATURE:
<223> OTHER INFORMATION: Synthetic Construct

<400> SEQUENCE: 11
caagtgcagt tggtgcagtc gggggcagaa gtgaaaaagc ccggcgcttc ggtgaaagtg      60
tcctgcaaag tgtccggcta ttctttgtcc aaatacgaca tgtcatgggt cagacaggct     120
cccggaaagg gtctggagtg gatggggatt atctatacat ccggctacac cgattacgcc     180
caaaagttcc aggggagagt caccatgact gaggatacgt ccaccgacac cgcctacatg     240
gaactgtcca gcctgcggtc cgaggacact gcggtgtact actgcgcgac cggaaaccca     300
tactacacca atggattcaa tagctgggga cagggtactc ttgtgacggt gtccagcgcc     360
tccaccaagg gcccatcggt cttcccgcta gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggacgagctg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctatagc aagctcaccg tggacaagag caggtggcag    1260
```

```
cagggaacg tcttctcatg ctccgtgatg catgaggctc tgcacaacca ctacacgcag    1320
aagagcctct ccctgtctcc gggtaaa                                       1347
```

<210> SEQ ID NO 12
<211> LENGTH: 651
<212> TYPE: DNA
<213> ORGANISM: Artificial Sequence
<220> FEATURE:
<223> OTHER INFORMATION: Synthetic Construct

<400> SEQUENCE: 12

```
gacatccaga tgacccagtc tccatcctcc ctgtctgcat ctgtgggaga cagagtcacc      60
atcacttgcc aggccagtca gagccctaat aacctcctgg cctggtatca gcagaaacca    120
gggaaagccc ctaagctcct gatctatggt gcatccgatc tgccatctgg ggtcccatca    180
aggttcagtg gcagtggatc tgggacagat ttcactctca ccatcagcag tctgcaacct    240
gaagattttg caacttacta ctgtcagaac aattattatg tgggaccagt gagctatgct    300
ttcggcggag ggaccaaggt ggagatcaag cggaccgtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagagtg c             651
```

<210> SEQ ID NO 13
<211> LENGTH: 288
<212> TYPE: PRT
<213> ORGANISM: Homo sapiens

<400> SEQUENCE: 13

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
            35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190
```

```
Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
                275                 280                 285

<210> SEQ ID NO 14
<211> LENGTH: 143
<212> TYPE: PRT
<213> ORGANISM: Homo sapiens

<400> SEQUENCE: 14

Leu Asp Ser Pro Asp Arg Pro Trp Asn Pro Pro Thr Phe Ser Pro Ala
1               5                   10                  15

Leu Leu Val Val Thr Glu Gly Asp Asn Ala Thr Phe Thr Cys Ser Phe
                20                  25                  30

Ser Asn Thr Ser Glu Ser Phe Val Leu Asn Trp Tyr Arg Met Ser Pro
            35                  40                  45

Ser Asn Gln Thr Asp Lys Leu Ala Ala Phe Pro Glu Asp Arg Ser Gln
        50                  55                  60

Pro Gly Gln Asp Cys Arg Phe Arg Val Thr Gln Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140

<210> SEQ ID NO 15
<211> LENGTH: 288
<212> TYPE: PRT
<213> ORGANISM: Macaca fascicularis

<400> SEQUENCE: 15

Met Gln Ile Pro Gln Ala Pro Trp Pro Val Val Trp Ala Val Leu Gln
1               5                   10                  15

Leu Gly Trp Arg Pro Gly Trp Phe Leu Glu Ser Pro Asp Arg Pro Trp
                20                  25                  30

Asn Ala Pro Thr Phe Ser Pro Ala Leu Leu Val Val Thr Glu Gly Asp
            35                  40                  45

Asn Ala Thr Phe Thr Cys Ser Phe Ser Asn Ala Ser Glu Ser Phe Val
        50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95
```

```
Val Thr Arg Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Ala Leu Val Gly Val Gly Gly
                165                 170                 175

Leu Leu Gly Ser Leu Val Leu Leu Val Trp Val Leu Ala Val Ile Cys
            180                 185                 190

Ser Arg Ala Ala Gln Gly Thr Ile Glu Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Ala Pro
225                 230                 235                 240

Cys Val Pro Glu Gln Thr Glu Tyr Ala Thr Ile Val Phe Pro Ser Gly
                245                 250                 255

Leu Gly Thr Ser Ser Pro Ala Arg Arg Gly Ser Ala Asp Gly Pro Arg
            260                 265                 270

Ser Pro Arg Pro Leu Arg Pro Glu Asp Gly His Cys Ser Trp Pro Leu
        275                 280                 285

<210> SEQ ID NO 16
<211> LENGTH: 143
<212> TYPE: PRT
<213> ORGANISM: Macaca fascicularis

<400> SEQUENCE: 16

Leu Glu Ser Pro Asp Arg Pro Trp Asn Ala Pro Thr Phe Ser Pro Ala
1               5                   10                  15

Leu Leu Leu Val Thr Glu Gly Asp Asn Ala Thr Phe Thr Cys Ser Phe
            20                  25                  30

Ser Asn Ala Ser Glu Ser Phe Val Leu Asn Trp Tyr Arg Met Ser Pro
        35                  40                  45

Ser Asn Gln Thr Asp Lys Leu Ala Ala Phe Pro Glu Asp Arg Ser Gln
    50                  55                  60

Pro Gly Gln Asp Cys Arg Phe Arg Val Thr Arg Leu Pro Asn Gly Arg
65                  70                  75                  80

Asp Phe His Met Ser Val Val Arg Ala Arg Arg Asn Asp Ser Gly Thr
                85                  90                  95

Tyr Leu Cys Gly Ala Ile Ser Leu Ala Pro Lys Ala Gln Ile Lys Glu
            100                 105                 110

Ser Leu Arg Ala Glu Leu Arg Val Thr Glu Arg Arg Ala Glu Val Pro
        115                 120                 125

Thr Ala His Pro Ser Pro Ser Pro Arg Pro Ala Gly Gln Phe Gln
    130                 135                 140

<210> SEQ ID NO 17
<211> LENGTH: 330
<212> TYPE: PRT
<213> ORGANISM: Homo sapiens
```

<400> SEQUENCE: 17

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 18
<211> LENGTH: 107
<212> TYPE: PRT
<213> ORGANISM: Homo sapiens

<400> SEQUENCE: 18

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

```
Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                      55                      60

Thr Tyr Ser Leu Ser Ser Thr Leu Thr Leu Ser Lys Ala Asp Tyr Glu
65                      70                      75                  80

Lys His Lys Val Tyr Ala Cys Glu Val Thr His Gln Gly Leu Ser Ser
                    85                      90                  95

Pro Val Thr Lys Ser Phe Asn Arg Gly Glu Cys
                100                 105

<210> SEQ ID NO 19
<211> LENGTH: 106
<212> TYPE: PRT
<213> ORGANISM: Homo sapiens

<400> SEQUENCE: 19

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
                20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
50                      55                      60

Lys Tyr Ala Ala Ser Ser Tyr Leu Ser Leu Thr Pro Glu Gln Trp Lys
65                      70                      75                  80

Ser His Arg Ser Tyr Ser Cys Gln Val Thr His Glu Gly Ser Thr Val
                    85                      90                  95

Glu Lys Thr Val Ala Pro Thr Glu Cys Ser
                100                 105
```

PD-1 AGONIST ANTIBODIES AND USES THEREOF

The present invention is in the field of medicine. More particularly, the present invention relates to agonistic antibodies directed to human programmed death 1 (PD-1; also known as CD279), compositions comprising such anti-human PD-1 agonistic antibodies, and methods of using such anti-human PD-1 agonistic antibodies for the treatment of autoimmune disorders or transplant rejection.

Immune checkpoint pathways modulate both the autoimmune response and the anti-cancer immune response (Isakov, N., *J. Autoimmune Disorders* 2016; 2(2):17). In autoimmune disease therapy, promoting, i.e., agonizing, the effect of an immune-inhibitory pathway, such that the immune response is suppressed, is desirable. Conversely, in cancer therapy, inhibiting, i.e., antagonizing, the effect of an immune-inhibitory pathway, such that the immune response is derepressed, or stimulated, is desirable.

PD-1 is a type I cell membrane protein. PD-1 belongs to the extended CD28/CTLA-4 family containing an extracellular IgV domain followed by a transmembrane and intracellular domain. Activation of the PD-1 pathway leads to inhibition of immune cell activation, such as reduced cellular proliferation, reduced cellular survival, and inhibition of inflammatory cytokines (e.g., IFNγ, TNFα and IL-2). PD-1 is expressed on recently activated immune cells, such as T cells, B cells, NKT cells, monocytes, and dendritic cells; and its expression is tightly regulated. The importance of PD-1 mediated signaling in modulating human immune response was demonstrated with the success of treating oncology patients with antagonist PD-1 antibodies. Cancer patients treated with a PD-1 antagonist antibody tend to have different autoimmune manifestations as a side-effect of the treatment (Cappelli, L. C., et al., 2017; Hoffman, L., et al., 2016). In addition, there are other known correlations between autoimmune disease activity and the PD-1 pathway. For example, SLE patients in flare tend to have low PD-L1 expression (Mozaffarian, N., et al., 2008) and autoantibodies to PD-1 (Shi, H., et al., 2017).

Therefore, increasing PD-1 mediated signaling constitutes a potential approach to manage autoimmune disorders that may lead to profound disease modification and durability of response along with key safety benefits over current immunomodulatory therapies. These current therapies, generally speaking, broadly down-regulate the body's immune system (e.g., corticosteroids and cyclophosphamide). However, PD-1 is expressed mostly on activated immune cells. Therefore, anti-PD-1 antibodies have the potential to selectively target cells that are activated during the time of treatment, leaving the rest of the immune cell repertoire intact.

The field has struggled to deliver PD-1 agonistic antibodies (Sharpe, A. and Pauken, E., *Nature Reviews Immunology* (2017)). The difficulty, at least partly, is thought to be the result of the complex cellular interactions required to achieve PD-1 agonism in physiological settings in vitro or in vivo. Therefore, the context of the assay or model used to identify therapeutic antibodies is clearly important when assessing PD-1 agonist antibody activity.

United States Patent Application Publication US20170088618 discloses anti-human PD-1 antibodies, which, in some embodiments, and in certain in vitro assays, behave as agonists with rates of association and dissociation with respect to the PD-1 extracellular domain resulting in $K_D$ values of between 19-22 nM (as determined by surface plasmon resonance (SPR) using a BIAcore® T200).

Thus, there exists a need for alternative anti-human PD-1 antibodies that 1) bind human PD-1 with desirable association and dissociation rates for optimal agonist activity, 2) agonize human PD-1 in an immunologically relevant context to achieve in vivo efficacy, 3) display sufficient potency as an monotherapy for the treatment and/or prevention of autoimmune disorders or the prevention of transplant rejection, 4) display desired activity as part of an combination therapy with other therapeutics for the treatment and/or prevention of autoimmune disorders or the prevention of transplant rejection, and/or 5) offers an effective alternative for drug switching when, during the treatment of an autoimmune disorder with another anti-human PD-1 agonist antibody, therapy is suspended because of at least one adverse event and/or inefficacy (particularly, anti-drug antibody (ADA) mediated reduction in efficacy).

Accordingly, the present invention provides novel humanized anti-human PD-1 agonist IgG1 antibodies. The antibodies of the present invention are particularly advantageous over prior art anti-PD-1 antibodies for various reasons, including, but not limited to, the following: 1) they bind human PD-1 (as well as cynomolgus monkey PD-1) with desirable association and dissociation rates, 2) they may be therapeutically effective at lower doses or less frequent dosing, 3) they inhibit primary human T cell proliferation in vitro, 4) they regulate human PD-1 cell surface expression, 5) they inhibit T cell receptor signaling activity in an in vitro NFAT reporter cell assay, 6) they have low therapeutic protein immunogenicity (i.e., anti-drug antibodies (ADA)) potential, 7) they reduce disease activity in a humanized GvHD model, and/or 8) in a lupus nephritis in vivo model, they inhibit immune cell activation:

a) without significant and/or detectable complement-dependent cytotoxicity, b) without competing with human PD-L1/2 for binding to human PD-1, c) without inducing significant and/or detectable cytokine release in in vitro assays.

Furthermore, exemplary anti-human PD-1 agonist IgG1 antibodies of the present invention also exhibit in vivo stability, physical and chemical stability, including, but not limited to, thermal stability, solubility, low self-association, and pharmacokinetic characteristics that are acceptable for development and/or use in the treatment of autoimmune disorders and/or transplant rejection (i.e., graft-versus host disease). Additionally, polynucleotide sequences disclosed herein that encode exemplary anti-human PD-1 agonist IgG1 antibodies of the present invention were engineered to use preferred codon to significantly improve expression of the antibodies in preferred mammalian cell line expression systems, such as CHO.

The subject invention provides an advance over the prior art by providing compositions and methods useful in the prevention, downregulation or amelioration of autoimmune and/or immune tolerance related disorders through immune checkpoint stimulation using a significantly engineered anti-human PD-1 agonist IgG1 antibody. The anti-human PD-1 agonist IgG1 antibodies of the present invention are capable of improving or restoring immune pathology, preferably, through inhibition of the adaptive arm of the immune response, abrogation of the antigen specific immune process and, thereby directly addressing the underlying disease pathology. The use of such antibodies clinically may prove to lead to long-term durability or remission of the disease(s) being treated.

The present disclosure provides an anti-human PD-1 antibody comprising: 1) a heavy chain variable region (HCVR) comprising an HCDR1 having the amino acid sequence of SEQ ID NO: 5, an HCDR2 having the amino acid sequence of SEQ ID NO: 6, an HCDR3 having the amino acid sequence of SEQ ID NO: 7; and 2) a light chain variable region (LCVR) comprising an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG isotype subclass 1 (IgG1).

In some embodiments, the present disclosure provides an anti-human PD-1 antibody comprising: 1) a HCVR having the amino acid sequence of SEQ ID NO: 3; and 2) a LCVR having the amino acid sequence of SEQ ID NO: 4, wherein the antibody is an IgG1.

In some embodiments, the present disclosure provides an anti-human PD-1 antibody comprising: 1) a heavy chain having the amino acid sequence of SEQ ID NO: 1; and 2) a light chain having the amino acid sequence of SEQ ID NO: 2.

In some embodiments, the present disclosure provides an anti-human PD-1 antibody consisting of two heavy chains having the amino acid sequence of SEQ ID NO: 1 and two light chains having the amino acid sequence of SEQ ID NO: 2.

The present disclosure also provides a mammalian cell capable of expressing an anti-human PD-1 antibody comprising: 1) a HCVR comprising an HCDR1 having the amino acid sequence of SEQ ID NO: 5, an HCDR2 having the amino acid sequence of SEQ ID NO: 6, an HCDR3 having the amino acid sequence of SEQ ID NO: 7; and 2) a LCVR comprising an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1.

In some embodiments, the present disclosure provides a mammalian cell capable of expressing an anti-human PD-1 antibody comprising: 1) a HCVR having the amino acid sequence of SEQ ID NO: 3; and 2) a LCVR having the amino acid sequence of SEQ ID NO: 4, wherein the antibody is an IgG1.

In some embodiments, the present disclosure provides a mammalian cell capable of expressing an anti-human PD-1 antibody comprising: 1) a heavy chain having the amino acid sequence of SEQ ID NO: 1; and 2) a light chain having the amino acid sequence of SEQ ID NO: 2. In some embodiments, the present disclosure provides that the anti-human PD-1 antibody consists of two heavy chains having the amino acid sequence of SEQ ID NO: 1 and two light chains having the amino acid sequence of SEQ ID NO: 2.

The present disclosure also provides a process for producing an anti-human PD-1 antibody, comprising: a) cultivating a mammalian cell capable of expressing the antibody, wherein the antibody comprises: 1) a HCVR comprising an HCDR1 having the amino acid sequence of SEQ ID NO: 5, an HCDR2 having the amino acid sequence of SEQ ID NO: 6, an HCDR3 having the amino acid sequence of SEQ ID NO: 7; and 2) a LCVR comprising an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1; and b) recovering the antibody.

In some embodiments, the present disclosure provides a process for producing an anti-human PD-1 antibody, comprising: a) cultivating a mammalian cell capable of expressing the antibody, wherein the antibody comprises: 1) a HCVR having the amino acid sequence of SEQ ID NO: 3; and 2) a LCVR having the amino acid sequence of SEQ ID NO: 4, wherein the antibody is an IgG1; and b) recovering the antibody.

In some embodiments, the present disclosure provides a process for producing an anti-human PD-1 antibody, comprising: a) cultivating a mammalian cell capable of expressing the antibody, wherein the antibody comprises: 1) a heavy chain having the amino acid sequence of SEQ ID NO: 1; and 2) a light chain having the amino acid sequence of SEQ ID NO: 2; and b) recovering the antibody.

In some embodiments, the present disclosure provides a process for producing an anti-human PD-1 agonist antibody, comprising: a) cultivating a mammalian cell capable of expressing the antibody, wherein the antibody consists of two heavy chains having the amino acid sequence of SEQ ID NO: 1 and two light chains having the amino acid sequence of SEQ ID NO: 2; and b) recovering the antibody.

The present disclosure also provides the anti-human PD-1 antibody produced by the aforementioned processes.

The present disclosure also provides a pharmaceutical composition comprising the anti-human PD-1 antibody produced by the aforementioned processes and an acceptable carrier, diluent, or excipient.

The present disclosure also provides a DNA molecule comprising a polynucleotide having the sequence of SEQ ID NO: 11, SEQ ID NO: 12, or SEQ ID NOs: 11 and 12. The present disclosure also provides a mammalian cell comprising a DNA molecule comprising a polynucleotide having the sequence of SEQ ID NO: 11, SEQ ID NO: 12, or SEQ ID NOs: 11 and 12.

The present disclosure provides a pharmaceutical composition comprising: 1) an anti-human PD-1 antibody comprising: a) a HCVR comprising an HCDR1 having the amino acid sequence of SEQ ID NO: 5, an HCDR2 having the amino acid sequence of SEQ ID NO: 6, an HCDR3 having the amino acid sequence of SEQ ID NO: 7; and b) a LCVR comprising an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1; and 2) an acceptable carrier, diluent, or excipient.

In some embodiments, the present disclosure provides a pharmaceutical composition comprising: 1) an anti-human PD-1 antibody comprising: a) a HCVR having the amino acid sequence of SEQ ID NO: 3; and b) a LCVR having the amino acid sequence of SEQ ID NO: 4, wherein the antibody is an IgG1; and 2) an acceptable carrier, diluent, or excipient.

The present disclosure provides a pharmaceutical composition comprising: 1) an anti-human PD-1 antibody comprising: a) a heavy chain having the amino acid sequence of SEQ ID NO: 1; and b) a light chain having the amino acid sequence of SEQ ID NO: 2; and 2) an acceptable carrier, diluent, or excipient. In some embodiments, the anti-human PD-1 antibody of the aforementioned pharmaceutical compositions consists of two heavy chains having the amino acid sequence of SEQ ID NO: 1 and two light chains having the amino acid sequence of SEQ ID NO: 2.

As used herein "PD-1" refers to programmed cell death 1, also known as programmed death 1 (PD-1; CD279), a type I cell membrane protein that belongs to the extended CD28/CTLA-4 family containing an extracellular IgV domain followed by a transmembrane and intracellular domain.

As used herein "hPD-1" or "human PD-1" refers to a wild-type human PD-1, preferably, a wild-type human PD-1 that has the amino acid sequence set forth in SEQ ID NO: 13 (i.e., NCBI Reference Sequence NP 005009.2).

The terms "cyno", "cynomolgus" or "cynomolgus monkey" are used interchangeably herein. When used in reference to a PD-1 polypeptide it is intended that the terms refer to wild-type cynomolgus monkey PD-1, and, preferably, a wild-type cynomolgus monkey PD-1 that has the amino acid sequence set forth in SEQ ID NO: 15.

A PD-1 polypeptide "extracellular domain" or "ECD" refers to a form of the PD-1 polypeptide that is essentially free of the transmembrane and cytoplasmic domains. Preferably, a PD-1 ECD has less than 1% of the transmembrane and cytoplasmic domain, more preferably, a PD-1 ECD has less than 0.5% of such domains. Even more preferably, human PD-1 ECD polypeptide is as shown in SEQ ID NO: 14 and cynomolgus monkey PD-1 ECD polypeptide is as shown in SEQ ID NO: 16. PD-1 polypeptide ECD may prepared using methods known in the art. Alternatively, human PD-1 polypeptide ECD may be purchased commercially from various vendors such as Sino Biological (Beijing, China; reference #10377-H08) and R&D Systems (Minneapolis, Minn., USA; cat. #8986-PD). Cynomolgus PD-1 polypeptide ECD may be purchased commercially from R&D Systems (Minneapolis, Minn., USA; cat. #8509-PD).

As used herein, "anti-human PD-1 agonist antibody" refers to an antibody that binds to human PD-1, and, when administered in vivo, results in at least one significantly lessened autoimmune activity such as reduction in anti-double stranded DNA (ds-DNA) titers, reduction in disease scores or reduction in inflammatory cytokines.

As used herein "Antibody 1" refers to a human PD-1 binding antibody comprising: 1) a HCVR having the HCDR1 amino acid sequence of SEQ ID NO: 5, the HCDR2 amino acid sequence of SEQ ID NO:6, the HCDR3 amino acid sequence of SEQ ID NO: 7; and 2) a LCVR having the LCDR1 amino acid sequence of SEQ ID NO: 8, the LCDR2 amino acid sequence of SEQ ID NO: 9, the LCDR3 amino acid sequence of SEQ ID NO: 10, the HCVR amino acid sequence of SEQ ID NO: 3, the LCVR amino acid sequence of SEQ ID NO: 4, the HC amino acid sequence of SEQ ID NO: 1, and the LC amino acid sequence of SEQ ID NO: 2.

The term "antibody" as used herein refers to an engineered, non-naturally occurring polypeptide complex having two heavy chains (HC) and two light chains (LC) such that the heavy chains and the light chains are interconnected by disulfide bonds, wherein the antibody is an IgG isotype antibody. As used herein with regard to antibodies of the present invention, the term "antibody" refers to an antibody which is an IgG isotype subclass 1 (i.e., IgG1), and has "heavy" chains and "light" chains that are cross-linked via intra- and inter-chain disulfide bonds. Light chains each form disulfide bonds with a heavy chain, and the two heavy chains form two disulfide bonds between each other. Each heavy chain is comprised of an N-terminal HCVR and a heavy chain constant region ("HCCR"). Each light chain is comprised of an N-terminal LCVR and a light chain constant region ("LCCR"). When expressed in certain biological systems, antibodies having native human Fc sequences are glycosylated in the Fc region. Typically, glycosylation occurs in the Fc region of the antibody at a highly conserved N-glycosylation site. N-glycans typically attach to asparagine. Antibodies may be glycosylated at other positions as well.

Preferably, antibodies of the present invention contain a Fc portion which is a human IgG1 subtype. It is well-known that human IgG1 binds to the Fc-gamma receptor family (FcγR) as well as C1q. Interaction with these receptors can induce antibody-dependent cell cytotoxicity (ADCC) and complement-dependent cytotoxicity (CDC).

The constant region of the heavy chains contains CH1, CH2, and CH3 domains. CH1 comes after the HCVR; the CH1 and HCVR form the heavy chain portion of a Fab. CH2 comes after the hinge region and before CH3. CH3 comes after CH2 and is at the carboxy-terminal end of the heavy chain. The constant region of the light chains contains one domain, CL. CL comes after the LCVR; the CL and LCVR form the light chain portion of a Fab. Preferably, the CL regions of the anti-human PD-1 agonist antibodies of the present invention are of the human kappa subtype (e.g., SEQ ID NO: 18).

A DNA molecule of the present invention is a DNA molecule that comprises a non-naturally occurring polynucleotide sequence encoding a polypeptide having the amino acid sequence of at least one of the polypeptides in an antibody of the present invention (e.g., heavy chain, light chain, variable heavy chain, and variable light chain).

The HCVR and LCVR regions of an antibody of the present invention can be further subdivided into regions of hyper-variability, termed complementarity determining regions ("CDRs"), interspersed with regions that are more conserved, termed framework regions ("FR"). Each HCVR and LCVR is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The Chothia CDR definitions are identical to the Kabat CDR definitions with the exception of HCDR1 and HCDR2. The North CDR definition (North et al., "A New Clustering of Antibody CDR Loop Conformations", Journal of Molecular Biology, 406, 228-256 (2011)) is based on affinity propagation clustering with a large number of crystal structures. For the purposes of the present invention, assignment of amino acids to CDR domains within the LCVR and HCVR regions of the antibodies of the present invention is based on the well-known Kabat numbering convention (Kabat, et al., Ann. NY Acad. Sci. 190:382-93 (1971); Kabat et al., Sequences of Proteins of Immunological Interest, Fifth Edition, U.S. Department of Health and Human Services, NIH Publication No. 91-3242 (1991)), and North numbering convention (North et al., A New Clustering of Antibody CDR Loop Conformations, Journal of Molecular Biology, 406:228-256 (2011)). In the case of the light chain CDRs of the antibodies of the present invention, the North CDR definitions are used. In the heavy chain both HCDR1 and HCDR3 also use the North definition. HCDR2 uses a hybrid of North and Kabat definitions. The North definition is used to identify the starting N-terminal site while Kabat is used to define the last position.

An isolated DNA encoding a HCVR region can be converted to a full-length heavy chain gene by operably linking the HCVR-encoding DNA to another DNA molecule encoding heavy chain constant regions. The sequences of human, as well as other mammalian, heavy chain constant region genes are known in the art. DNA fragments encompassing these regions can be obtained, e.g., by standard PCR amplification.

An isolated DNA encoding a LCVR region may be converted to a full-length light chain gene by operably linking the LCVR-encoding DNA to another DNA molecule encoding a light chain constant region. The sequences of human, as well as other mammalian, light chain constant region genes are known in the art. DNA fragments encompassing these regions can be obtained by standard PCR amplification. The light chain constant region can be a kappa or lambda constant region. Preferably, for antibodies of the present invention, the light chain constant region is a kappa constant region.

The polynucleotides of the present invention can be expressed in a host cell after the sequences have been operably linked to an expression control sequence. The expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

The antibodies of the present invention can readily be produced in mammalian cells, non-limiting examples of which includes CHO, NSO, HEK293 or COS cells. The host cells are cultured using techniques well known in the art.

The vectors containing the polynucleotide sequences of interest (e.g., the polynucleotides encoding the polypeptides of the antibody and expression control sequences) can be transferred into the host cell by well-known methods, which vary depending on the type of cellular host.

Various methods of protein purification may be employed to purify proteins, including, but not limited to, antibodies and such methods are known in the art.

In other embodiments of the present invention, the antibody, or the nucleic acids encoding the same, is provided in isolated form. As used herein, the term "isolated" refers to a protein, peptide, or nucleic acid which is free or substantially free from any other macromolecular species found in a cellular environment. "Substantially free" as used herein means the protein, peptide, or nucleic acid of interest comprises more than 80% (on a molar basis) of the macromolecular species present, preferably more than 90%, and more preferably more than 95%.

An antibody of the present invention, or a pharmaceutical composition comprising the same, may be administered by parenteral routes, non-limiting examples of which are subcutaneous administration and intravenous administration. An antibody of the present invention may be administered to a patient alone with pharmaceutically acceptable carriers, diluents, or excipients in single or multiple doses. Pharmaceutical compositions of the present invention can be prepared by methods well known in the art (e.g., Remington: The Science and Practice of Pharmacy, 22nd ed. (2012), A. Loyd et al., Pharmaceutical Press) and comprise an antibody, as disclosed herein, and one or more pharmaceutically acceptable carriers, diluents, or excipients.

As used herein, the term "autoimmune disease" or "autoimmune disorder" are used interchangeably herein and refer to undesirable conditions that arise from an inappropriate or unwanted immune reaction against self-cells and/or tissues or transplanted cells and/or tissues. The term "autoimmune disease" or "autoimmune disorder" is meant to include such conditions, whether they be mediated by humoral or cellular immune responses. Exemplary autoimmune diseases or disorders include, but are not limited to, graft-versus-host disease (GVHD), solid organ transplantation rejection, vasculitis, systemic lupus erythematosus (SLE), type 1 diabetes mellitus (T1DM), multiple sclerosis (MS), giant cell arteritis (GCA), psoriasis (PsO), psoriatic arthritis (PsA), rheumatoid arthritis (RA), inflammatory bowel disease (IBD), ulcerative colitis (UC), ankylosing spondylitis (AS), Sjogren's syndrome (SjS), autoimmune hepatitis, scleroderma, celiac disease, Addison's disease, Hashimoto's disease, Graves' disease, atrophic gastritis/pernicious anemia, acquired hypogonadism/infertility, hypoparathyroidism, Coombs positive-hemolytic anemia, chronic allergic diseases (such as asthma, hay fever, or allergic rhinitis), Crohn's disease, male or female infertility, Behcet's, Wegener's granulomatosis, myocarditis, myositis, polymyalgia rheumatic (PMR), spontaneous abortion, vitiligo, atherosclerosis, autoimmune pancreatitis, bullous pemphigoid, chronic viral infections, and myasthenia gravis. For purposes of the present disclosure, preferred autoimmune diseases are graft-versus-host disease (GVHD), solid organ transplantation rejection, vasculitis, systemic lupus erythematosus (SLE), type 1 diabetes mellitus (T1DM), multiple sclerosis (MS), giant cell arteritis (GCA), psoriasis (PsO), psoriatic arthritis (PsA), rheumatoid arthritis (RA), inflammatory bowel disease (IBD), ulcerative colitis (UC), ankylosing spondylitis (AS), Sjogren's syndrome (SjS), autoimmune hepatitis, and scleroderma.

As used herein the term "about" implies plus or minus ten percent of the stated value or range of values. For example: "about" 12, includes values ranging from 10.8 (inclusive) to 13.2 (inclusive); about 10 wt. percent encompasses formation that include between 9 (inclusive) to 11 (inclusive) wt. percent; and the like.

"Binds" as used herein in reference to the affinity of an anti-human PD-1 agonist IgG1 antibody for human PD-1 (SEQ ID NO: 13) or human PD-1 ECD, preferably, the human PD-1 ECD as shown in SEQ ID NO: 14, is intended to mean, unless indicated otherwise, a $K_D$ of about $1\times10^{-7}$ M, of about $1\times10^{-8}$M, of about $1\times10^{-9}$M, of about $5\times10^{-9}$ M, about $1\times10^{-10}$ M as determined by methods known in the art and/or by methods essentially as described herein, including, but not limited to, use of a surface plasmon resonance (SPR) biosensor at 25° C. or 37° C. More preferably, an anti-human PD-1 agonist IgG1 antibody of the present invention binds human PD-1 (i.e., SEQ ID NO: 13) or human PD-1 ECD (e.g., SEQ ID NO: 14), with a $K_D$ of between about $1\times10^{-8}$M and about $5\times10^{-10}$ M as determined by methods known in the art and/or by methods essentially as described herein, including by use of a SPR biosensor at 25° C. or 37° C. Even more preferably, such an antibody will have an affinity for human PD-1 (i.e., SEQ ID NO: 13) or human PD-1 ECD (e.g., SEQ ID NO: 14), of between about $5\times10^{-8}$M and about $5\times10^{-10}$ M as determined by methods known in the art and/or by methods essentially as described herein, including by use of a SPR biosensor at 25° C. or 37° C. Even more preferably, such an antibody will have Kon and Koff values for human PD-1 ECD (e.g., SEQ ID NO: 14) of about $1.0\times10^{-4}$ to about $1.0\times10^{-3}$ and about $1.3\times10^{5}$ to about $2.0\times10^{5}$, respectively (as determined by SPR using on BIAcore® 8K essentially as described herein).

In the context of monoclonal antibodies, the terms "human," "humanized" and "fully human" are well known to those of ordinary skill in the art (Weiner L J, *J. Immunother.* 2006; 29: 1-9; Mallbris L, et al., *J. Clin. Aesthet. Dermatol.* 2016; 9: 13-15).

As used herein, the term "adaptive immunity" includes the arm of the immune response which, in contrast to the innate arm of the immune response is antigen specific and shows enhanced, secondary antigen-specific immune responses upon re-stimulation with the same antigen.

The term "treating" (or "treat" or "treatment") refers to slowing, interrupting, arresting, alleviating, stopping, reducing, or reversing the progression or severity of an existing symptom, disorder, condition, or disease.

"Effective amount" means the amount of an anti-human PD-1 agonist IgG1 antibody of the present invention or pharmaceutical composition comprising such an antibody that will elicit the biological or medical response of or desired therapeutic effect on a tissue, system, animal, mammal or human that is being sought by the researcher, medical doctor, or other clinician. An effective amount of the antibody may vary according to factors such as the disease state, age, sex, and weight of the individual, and the ability of the antibody to elicit a desired response in the individual. An effective amount is also one in which any toxic or detrimental effect of the antibody is outweighed by the therapeutically beneficial effects. Such benefit includes any one or more of: an increased immune tolerance of transplanted organs; stabilized autoimmune disease or disorder; or improving signs or symptoms of an autoimmune disorder, etc. An effective amount can be readily determined by one skilled in the art, by the use of known techniques, and by observing results obtained under analogous circumstances. In determining the effective amount for a patient, a number of factors are considered by the attending diagnostician, including, but not limited to: the patient's size, age, and general health; the specific disease or disorder involved; the degree of, or involvement, or the severity of the disease or disorder; the response of the individual patient; the particular compound administered; the mode of administration; the bioavailability characteristics of the preparation administered; the dose regimen selected; the use of concomitant medication; and other relevant circumstances.

As used herein, the term "effective response" of a patient or a patient's "responsiveness" to treatment refers to the clinical or therapeutic benefit imparted to a patient upon administration an antibody of the present disclosure. Such benefit includes any one or more of the following: an increased immune tolerance of transplanted organs; stabilized autoimmune disease or disorder; or improving signs or symptoms of an autoimmune disorder, etc.

A potential advantage of methods disclosed herein is the possibility of producing marked and/or prolonged relief in a patient suffering from an autoimmune disorder with an acceptable safety profile including acceptable tolerability, toxicities and/or adverse events, so that the patient benefits from the treatment method overall. The efficacy of the treatment of the present disclosure can be measured by various endpoints that are commonly used in evaluating treatments for various autoimmune disorders including, but not limited to, American College of Rheumatology (ACR) 20, ACR50, ACR70, Psoriasis Area and Severity Index (PAST) 50, PASI75, PASI90, PASI100, Systemic Lupus Erythmatosus Disease Activity Index (SLEDAI). Various other approaches to determining efficacy of any particular therapy of the present invention can be optionally employed, including, for example, immune cell activation markers, measures of inflammation, cell-cycle dependent biomarkers measurement visualization, and/or measurement of response through pain assessments.

Anti-drug antibody formation to biologics can reduce the effectiveness of a treatment due to formation of neutralizing antibodies or faster pharmacokinetics. In some rare instances, ADAs can also be associated with safety issues. Autoimmune diseases are chronic, requiring long-term treatment. Therefore, there often is a need for alternative treatments when a therapeutic biological drug (e.g., therapeutic antibody) stops working. In order to overcome challenges with immunogenicity over time, sequential use of biologics, even ones targeting the same target, e.g. TNF inhibitors, is a widely accepted and utilized treatment practice in autoimmune space (see, for example, Lloyd, S., et al. (2010) The effectiveness of anti-TNFα therapies when used sequentially in rheumatoid arthritis patients: a systematic review and meta-analysis. Rheumatology, 49:2313-21).

The present disclosure provides an anti-human PD-1 antibody comprising:

1) a HCVR comprising an HCDR1 having the amino acid sequence of SEQ ID NO: 5, an HCDR2 having the amino acid sequence of SEQ ID NO: 6, an HCDR3 having the amino acid sequence of SEQ ID NO: 7; and 2) a LCVR comprising an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1. Preferably, such an antibody binds human PD-1 (i.e., SEQ ID NO: 13) or human PD-1 ECD (e.g., SEQ ID NO: 14), with a $K_D$ of about $1\times10^{-7}$M, of about $1\times10^{-8}$M, of about $1\times10^{-9}$M, of about $5\times10^{-9}$M, or of about $1\times10^{-10}$ M as determined by methods known in the art and/or by methods essentially as described herein, including, but not limited to, use of a surface plasmon resonance (SPR) biosensor at 25° C. or 37° C. Preferably, such an antibody binds human PD-1 (i.e., SEQ ID NO: 13) or human PD-1 ECD (e.g., SEQ ID NO: 14), with a $K_D$ of between about $1\times10^{-8}$ M and about $5\times10^{-10}$ M as determined by methods known in the art and/or by methods essentially as described herein, including, but not limited to, use of a surface plasmon resonance (SPR) biosensor at 25° C. or 37° C. More preferably, such an antibody binds human PD-1 (i.e., SEQ ID NO: 13) or human PD-1 ECD (e.g., SEQ ID NO: 14), with a $K_D$ of between about $5\times10^{-8}$M and about $5\times10^{-10}$ M as determined by methods known in the art and/or by methods essentially as described herein, including, but not limited to, use of a surface plasmon resonance (SPR) biosensor at 25° C. or 37° C.

In some embodiments, the present disclosure provides an anti-human PD-1 antibody comprising:

1) a HCVR having the amino acid sequence of SEQ ID NO: 3; and 2) a LCVR having the amino acid sequence of SEQ ID NO: 4, wherein the antibody is an IgG1. Preferably, such an antibody binds human PD-1 (i.e., SEQ ID NO: 13) or human PD-1 ECD (e.g., SEQ ID NO: 14), with a $K_D$ of about $1\times10^{-7}$ M, of about $1\times10^{-8}$M, of about $1\times10^{-9}$M, of about $5\times10^{-9}$M, or of about $1\times10^{-10}$ M as determined by methods known in the art and/or by methods essentially as described herein, including, but not limited to, use of a surface plasmon resonance (SPR) biosensor at 25° C. or 37° C. More preferably, such an antibody binds human PD-1 (i.e., SEQ ID NO: 13) or human PD-1 ECD (e.g., SEQ ID NO: 14), with a $K_D$ of between about $1\times10^{-8}$M and about $5\times10^{-10}$ M as determined by methods known in the art and/or by methods essentially as described herein, including, but not limited to, use of a surface plasmon resonance (SPR) biosensor at 25° C. or 37° C. Even more preferably, such an antibody binds human PD-1 (i.e., SEQ ID NO: 13) or human PD-1 ECD (e.g., SEQ ID NO: 14), with a $K_D$ of between about $5 \times 10^{-8}$M and about $5 \times 10^{-10}$ M as determined by methods known in the art and/or by methods essentially as described herein, including, but not limited to, use of a surface plasmon resonance (SPR) biosensor at 25° C. or 37° C.

In some embodiments, the present disclosure provides an anti-human PD-1 antibody comprising:

1) a heavy chain having the amino acid sequence of SEQ ID NO: 1; and 2) a light chain having the amino acid sequence of SEQ ID NO: 2. In some embodiments, the present disclosure provides an anti-human PD-1 antibody consisting of two heavy chains having the amino acid sequence of SEQ ID NO: 1 and two light chains having the amino acid sequence of SEQ ID NO: 2. Preferably, such an antibody binds human PD-1 (i.e., SEQ ID NO: 13) or human PD-1 ECD (e.g., SEQ ID NO: 14), with a $K_D$ of about $1 \times 10^{-7}$ M, of about $1 \times 10^{-8}$M, of about $1 \times 10^{-9}$ M, of about $5 \times 10^{-9}$M, of about $1 \times 10^{-10}$ M as determined by methods known in the art and/or by methods essentially as described herein, including, but not limited to, use of a surface plasmon resonance (SPR) biosensor at 25° C. or 37° C. More preferably, such an antibody binds human PD-1 (i.e., SEQ ID NO: 13) or human PD-1 ECD (e.g., SEQ ID NO: 14), with a $K_D$ of between about $1 \times 10^{-8}$M and about $5 \times 10^{-10}$ M as determined by methods known in the art and/or by methods essentially as described herein, including, but not limited to, use of a surface plasmon resonance (SPR) biosensor at 25° C. or 37° C. Even more preferably, such an antibody binds human PD-1 (i.e., SEQ ID NO: 13) or human PD-1 ECD (e.g., SEQ ID NO: 14), with a $K_D$ of between about $5 \times 10^{-8}$M and about $5 \times 10^{-10}$ M as determined by methods known in the art and/or by methods essentially as described herein, including, but not limited to, use of a surface plasmon resonance (SPR) biosensor at 25° C. or 37° C.

The present disclosure provides a mammalian cell capable of expressing an anti-human PD-1 antibody comprising: an HCDR1 having the amino acid sequence of SEQ ID NO: 5, an HCDR2 having the amino acid sequence of SEQ ID NO: 6, an HCDR3 having the amino acid sequence of SEQ ID NO: 7, an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1.

In some embodiments, the present disclosure provides a mammalian cell capable of expressing an anti-human PD-1 antibody comprising a HCVR having the amino acid sequence of SEQ ID NO: 3 and a LCVR having the amino acid sequence of SEQ ID NO: 4, wherein the antibody is an IgG1.

In some embodiments, the present disclosure provides a mammalian cell capable of expressing an anti-human PD-1 antibody comprising an anti-human PD-1 antibody comprising a heavy chain having the amino acid sequence of SEQ ID NO: 1 and a light chain having the amino acid sequence of SEQ ID NO: 2. In some embodiments, the present disclosure provides a mammalian cell capable of expressing an anti-human PD-1 antibody comprising an anti-human PD-1 antibody consisting of two heavy chains having the amino acid sequence of SEQ ID NO: 1 and two light chains having the amino acid sequence of SEQ ID NO: 2.

The present disclosure provides a process for producing an anti-human PD-1 antibody, comprising: 1) cultivating a mammalian cell capable of expressing an anti-human PD-1 antibody comprising an HCDR1 having the amino acid sequence of SEQ ID NO: 5, an HCDR2 having the amino acid sequence of SEQ ID NO: 6, an HCDR3 having the amino acid sequence of SEQ ID NO: 7, an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1; and 2) recovering the antibody.

In some embodiments, the present disclosure provides a process for producing an anti-human PD-1 antibody comprising: 1) cultivating a mammalian cell capable of expressing an anti-human PD-1 antibody comprising a HCVR having the amino acid sequence of SEQ ID NO: 3 and a LCVR having the amino acid sequence of SEQ ID NO: 4, wherein the antibody is an IgG1, and 2) recovering the antibody.

In some embodiments, the present disclosure provides a process for producing an anti-human PD-1 antibody, comprising: 1) cultivating a mammalian cell capable of expressing an anti-human PD-1 antibody comprising a heavy chain having the amino acid sequence of SEQ ID NO: 1 and a light chain having the amino acid sequence of SEQ ID NO: 2; and 2) recovering the antibody. In some embodiments, the present disclosure provides a process for producing an anti-human PD-1 antibody, comprising: 1) cultivating a mammalian cell capable of expressing an anti-human PD-1 antibody consisting of two heavy chains having the amino acid sequence of SEQ ID NO: 1 and two light chains having the amino acid sequence of SEQ ID NO: 2; and 2) recovering the antibody. The present disclosure also provides the anti-human PD-1 antibody produced by the process and an acceptable carrier, diluent, or excipient.

The present disclosure provides a DNA molecule comprising a polynucleotide having the sequence of SEQ ID NO: 11, SEQ ID NO: 12, or SEQ ID NOs: 11 and 12. The present disclosure also provides a mammalian cell comprising a DNA molecule comprising a polynucleotide having the sequence of SEQ ID NO: 11, SEQ ID NO: 12, or SEQ ID NOs: 11 and 12.

The present disclosure provides a pharmaceutical composition comprising 1) an anti-human PD-1 antibody, comprising an HCDR1 having the amino acid sequence of SEQ ID NO: 5, an HCDR2 having the amino acid sequence of SEQ ID NO: 6, an HCDR3 having the amino acid sequence of SEQ ID NO: 7, an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1, and 2) an acceptable carrier, diluent, or excipient. In some embodiments, the anti-human PD-1 antibody comprises a HCVR having the amino acid sequence of SEQ ID NO: 3 and a LCVR having the amino acid sequence of SEQ ID NO: 4, wherein the antibody is an IgG1. In some embodiments, the anti-human PD-1 antibody comprises a heavy chain having the amino acid sequence of SEQ ID NO: 1 and a light chain having the amino acid sequence of SEQ ID NO: 2. In some embodiments, the anti-human PD-1 antibody consists of two heavy chains having the amino acid sequence of SEQ ID NO: 1 and two light chains having the amino acid sequence of SEQ ID NO: 2.

The role of the PD-1 pathway as a checkpoint for immunity has been extensively studied. It is known when the PD-1 pathway is stimulated, immune system activity generally decreases, which can be exploited for treatment of autoimmune disorders, induce immune tolerance, and/or reduce graft-versus-host disease.

The present disclosure provides a method of treating an autoimmune disorder, comprising administering to a patient in need thereof an effective amount of an anti-human PD-1 antibody comprising: 1) a HCVR comprising an HCDR1 having the amino acid sequence of SEQ ID NO: 5, an HCDR2 having the amino acid sequence of SEQ ID NO: 6, an HCDR3 having the amino acid sequence of SEQ ID NO: 7; and 2) a LCVR comprising an LCDR1 having the amino acid sequence of SEQ ID NO: 8, an LCDR2 having the amino acid sequence of SEQ ID NO: 9, and an LCDR3 having the amino acid sequence of SEQ ID NO: 10, wherein the antibody is an IgG1. In some embodiments, the present disclosure provides a method of treating an autoimmune disorder, comprising administering to a patient in need thereof an effective amount of an anti-human PD-1 antibody comprising: 1) a HCVR having the amino acid sequence of SEQ ID NO: 3; and 2) a LCVR having the amino acid sequence of SEQ ID NO: 4, wherein the antibody is an IgG1. In some embodiments, the present disclosure provides a method of treating an autoimmune disorder, comprising administering to a patient in need thereof an effective amount of an anti-human PD-1 antibody comprising: 1) a heavy chain having the amino acid sequence of SEQ ID NO: 1 and 2) a light chain having the amino acid sequence of SEQ ID NO: 2. In some embodiments, the present disclosure also provides that the antibody consists of two heavy chain having the amino acid sequence of SEQ ID NO: 1 and two light chains having the amino acid sequence of SEQ ID NO: 2. In such embodiments, the present disclosure also provides that the autoimmune disorder is GVHD, solid organ transplantation rejection, vasculitis, SLE, T1DM, MS, GCA, PsO, PsA, RA, IBD, UC, AS, SjS, autoimmune hepatitis, scleroderma, celiac disease, Addison's disease, Hashimoto's disease, Graves' disease, atrophic gastritis/pernicious anemia, acquired hypogonadism/infertility, hypoparathyroidism, Coombs positive-hemolytic anemia, chronic allergic diseases (such as asthma, hay fever, or allergic rhinitis), Crohn's disease, male or female infertility, Behcet's, Wegener's granulomatosis, myocarditis, myositis, PMR, spontaneous abortion, vitiligo, atherosclerosis, autoimmune pancreatitis, bullous pemphigoid, chronic viral infections, or myasthenia gravis.

In some embodiments, the present disclosure also provides that the antibody is administered in combination with other therapeutic agents used for the treatment of autoimmune disorders.

The present disclosure provides an anti-human PD-1 antibody of the present invention, for use in therapy. In some embodiments, the present disclosure provides an anti-human PD-1 antibody comprising: 1) a HCVR having the amino acid sequence of SEQ ID NO: 3; and 2) a LCVR having the amino acid sequence of SEQ ID NO: 4, wherein the antibody is an IgG1, for use in therapy. In some embodiments, the present disclosure provides an anti-human PD-1 antibody comprising: 1) a heavy chain having the amino acid sequence of SEQ ID NO: 1 and a light chain having the amino acid sequence of SEQ ID NO: 2, for use in therapy. In some embodiments, the present disclosure also provides that the antibody consists of two heavy chain having the amino acid sequence of SEQ ID NO: 1 and two light chains having the amino acid sequence of SEQ ID NO: 2. In some embodiments, the present disclosure provides that the therapy is for the treatment of an autoimmune disorder. In some embodiments, the present disclosure provides the autoimmune disorder is GVHD, solid organ transplantation rejection, vasculitis, SLE, T1DM, MS, GCA, PsO, PsA, RA, IBD, UC, AS, SjS, autoimmune hepatitis, scleroderma, celiac disease, Addison's disease, Hashimoto's disease, Graves' disease, atrophic gastritis/pernicious anemia, acquired hypogonadism/infertility, hypoparathyroidism, Coombs positive-hemolytic anemia, chronic allergic diseases (such as asthma, hay fever, or allergic rhinitis), Crohn's disease, male or female infertility, Behcet's, Wegener's granulomatosis, myocarditis, myositis, PMR, spontaneous abortion, vitiligo, atherosclerosis, autoimmune pancreatitis, bullous pemphigoid, chronic viral infections, or myasthenia gravis. In some embodiments, the present disclosure provides that the antibody is administered in combination with another therapeutic agent for treating the autoimmune disorder. In some embodiments, the present disclosure also provides that the antibody is (or is to be) administered in simultaneous, separate, or sequential combination with another therapeutic agent for treating the autoimmune disorder.

The present disclosure provides an anti-human PD-1 antibody of the present invention, for the manufacture of a medicament for the treatment of an autoimmune disorder. In some embodiments, the present disclosure provides an anti-human PD-1 antibody comprising: 1) a HCVR having the amino acid sequence of SEQ ID NO: 3; and 2) a LCVR having the amino acid sequence of SEQ ID NO: 4, wherein the antibody is an IgG1, for the manufacture of a medicament for the treatment of an autoimmune disorder. In some embodiments, the present disclosure provides an anti-human PD-1 antibody comprising: 1) a heavy chain having the amino acid sequence of SEQ ID NO: 1; and 2) a light chain having the amino acid sequence of SEQ ID NO: 2, for the manufacture of a medicament for the treatment of an autoimmune disorder. In some embodiments, the present disclosure also provides that the antibody consists of two heavy chain having the amino acid sequence of SEQ ID NO: 1 and two light chains having the amino acid sequence of SEQ ID NO: 2. In one embodiment, the present disclosure provides that the medicament is for the treatment of an autoimmune disorder. In some embodiments, the present disclosure provides that the medicament is for the treatment of GVHD, solid organ transplantation rejection, vasculitis, SLE, T1DM, MS, GCA, PsO, PsA, RA, IBD, UC, AS, SjS, autoimmune hepatitis, scleroderma, celiac disease, Addison's disease, Hashimoto's disease, Graves' disease, atrophic gastritis/pernicious anemia, acquired hypogonadism/infertility, hypoparathyroidism, Coombs positive-hemolytic anemia, chronic allergic diseases (such as asthma, hay fever, or allergic rhinitis), Crohn's disease, male or female infertility, Behcet's, Wegener's granulomatosis, myocarditis, myositis, PMR, spontaneous abortion, vitiligo, atherosclerosis, autoimmune pancreatitis, bullous pemphigoid, chronic viral infections, or myasthenia gravis.

Dosage regimens may be adjusted to provide the optimum desired response (e.g., a therapeutic effect). Treatment dosages may be titrated to optimize safety and efficacy. Dosing schedules, for intravenous (i.v.) or non-intravenous administration, subcutaneous (s.c.) localized or systemic, or combinations thereof, will typically range from a single bolus dosage or continuous infusion to multiple subcutaneous administrations per month, preferably, no more than once per day, more preferably, no more than once per week, even more preferably no more than once per every two weeks, even more preferably, no more than once per month or as indicated by the treating physician and the patient's condition. Dosing amounts and frequencies may be determined by the physician(s) treating the patient.

EXAMPLE 1: ANTIBODY EXPRESSION AND PURIFICATION

The amino acid sequences of the CDRs of the variable region of the heavy chain and light chain, the complete heavy chain and light chain amino acid sequences of Antibody 1, and the nucleotide sequences encoding the same, are listed below in the section entitled "Amino Acid and Nucleotide Sequences." In addition, the SEQ ID NOs of the amino acid sequences of the light chain, heavy chain, LCVR, and HCVR of Antibody 1 are shown in Table 1(a) below. Furthermore, the SEQ ID NOs for the amino acid sequences of the CDRs of the HC variable region and LC variable region of Antibody 1 are shown in Table 1(a).

The antibodies of the present invention, including, but not limited to, Antibody 1, can be made and purified essentially as follows. An appropriate host cell such as, but not limited to, HEK 293 or CHO, can be either transiently or stably transfected with an expression system for secreting antibodies using, for example, a single vector encoding for the expression of the heavy chain and the light chain or two vectors, one which encodes the heavy chain and one that encodes the light chain (using an optimal predetermined HC:LC vector ratio (such as 1:3 or 1:2).

Because efficient expression of therapeutic antibodies in mammalian cells is often a critical factor for commercial success of a therapeutic antibody, cDNA encoding Antibody 1 was optimized by testing multiple codon variants, including some obtained from commercially available codon optimization services for the signal sequence and variable regions. Polynucleotides as shown in SEQ ID NOs: 11 and 12 encoding the heavy and light chain of Antibody 1, respectively, were used to generate a cell line that efficiently produces increased titers (e.g., preferably, up to about 6-fold, more preferably, up to about 7-fold, even more preferably, up to about 8-fold, even more preferably, up to about 9-fold, even more preferably, up to 10-fold, even more preferably up to 11-fold more) compared to a similar CHO cell line expressing a polynucleotide as shown in SEQ ID NO:12 and a polynucleotide encoding the heavy chain of Antibody 1 that was not optimized with regard to codon usage in a stable CHO cell line.

Media, into which the Antibody 1 has been secreted, may be purified using any of many commonly-used techniques. For example, the medium may be applied to a Mab Select column (GE Healthcare), or KappaSelect column (GE Healthcare) for Fab fragment, that has been equilibrated with a compatible buffer, such as phosphate buffered saline (pH 7.4). The column may be washed to remove nonspecific binding components. The bound antibody may be eluted, for example, by pH gradient (such as 20 mM Tris buffer, pH 7, to 10 mM sodium citrate buffer, pH 3.0, or phosphate buffered saline, pH 7.4, to 100 mM glycine buffer, pH 3.0). Antibody fractions may be detected, such as by UV absorption or SDS-PAGE, and then may be pooled. Soluble aggregate and multimers may be effectively removed by common techniques, including size exclusion, hydrophobic interaction, ion exchange, multimodal, or hydroxyapatite chromatography. The antibody may be concentrated, buffer exchanged, and/or sterile filtered using common techniques. The product may be stored at 4-5° C. or immediately frozen at −80° C. or may be lyophilized.

TABLE 1(a)

SEQ ID NOs for anti-human PD-1 Agonist Antibody Antibody 1

| Amino Acid Sequence for: | SEQ ID NO: |
|---|---|
| Heavy chain | 1 |
| Light chain | 2 |
| HCVR | 3 |
| LCVR | 4 |
| HCDR1 | 5 |
| HCDR2 | 6 |
| HCDR3 | 7 |
| LCDR1 | 8 |
| LCDR2 | 9 |
| LCDR3 | 10 |
| DNA Sequence encoding for: | |
| HC | 11 |
| LC | 12 |

TABLE 1(b)

SEQ ID NOs for PD-1 Sequences

| Amino Acid Sequence for: | SEQ ID NO: |
|---|---|
| Human PD-1 | 13 |
| Human PD-1 ECD | 14 |
| Cynomolgus Monkey PD-1 | 15 |
| Cynomolgus Monkey PD-1 ECD | 16 |

EXAMPLE 2: ANTIBODY 1 BINDS TO HUMAN AND CYNOMOLGUS MONKEY PD-1 ON CELL SURFACE

The ability of the anti-human PD-1 agonist antibodies disclosed herein to bind to cell surface human or cynomolgus monkey PD-1 can be measured using a flow cytometric assay. Human and cynomolgus monkey PD-1 (i.e., as shown in SEQ ID NOs: 13 and 15, respectively) expressing stable cells are generated by transfecting human or cynomolgus monkey PD-1 plasmid DNA into Chinese Hamster Ovary cells (CHO-k1; Lonza) using an electroporation system (Gene Pulser Xcell; BioRad) according to established protocols. Stable cells are selected from single isolated cells using 500 µg/mL G418 (Thermo Scientific) in culture medium. For flow cytometry, the cells are transferred into a 96-well V-bottom plate at density of $1 \times 10^5$ cells/well. The cells are washed with 1×FACS buffer (Becton Dickinson #554656). Antibody 1, or control human IgG1 (diluted in FACS buffer in a three-fold 12-point titration of the antibodies, starting at 100 micrograms/mL) are added (in 100 microliters) and cells are incubated at 4° C. for 30 minutes. After washing twice in FACS buffer, FITC conjugated F(ab')$_2$ fragment goat anti-human IgG, Fcγ fragment specific secondary antibody (Jackson ImmunoResearch Laboratories 109-096-170) is added at a 1:200 dilution and the cells are incubated at 4° C. for 30 minutes. After washing twice in FACS buffer, live/dead cell staining is performed using SytoxBlue (Invitrogen, #S34857) per manufacturer's protocol. Cells are processed on Fortessa, Fortessa Fx or LSRII flow cytometry instrument. Flow cytometry data is analyzed using FlowJo software. Geometric Mean Fluorescence Intensity (GMFI) values are used to calculate relative $EC_{50}$ based on 4-parameter logistic regression.

In experiments performed essentially as described above, Antibody 1 was able to bind cell membrane expressed human or cynomolgus monkey PD-1 with an average $EC_{50}$ of 1.30+/−0.16 µg/mL and 1.09+/−0.30 µg/mL, respectively. This data demonstrate that Antibody 1 is able to bind both human and cynomolgus monkey membrane bound PD-1 with similar affinity.

EXAMPLE 3: ANTIBODY 1 BINDING KINETICS/AFFINITY FOR HUMAN AND CYNOMOLGUS MONKEY PD-1 ECD

The binding kinetics of an anti-human PD-1 agonist antibody of the invention to human and cynolmolgus monkey PD-1 ECDs may be determined by use of a surface plasmon resonance biosensor such as BIAcore® 2000, BIAcore® 3000, BIAcore® 8K, or a BIAcore® T100 (GE Healthcare, Piscataway, N.J.). Briefly described, a BIAcore® 8K instrument is used to measure the binding kinetics for Antibody 1 to human and cynomolgus monkey PD1-extracellular domain (ECD)-His via surface plasmon resonance (SPR) at 25° C. Samples are dissolved in 1×HBS-EP+ running buffer (Teknova cat. # H8022) and a protein A coupled CMS Series S sensor chip (GE Healthcare Cat #29139131-AA) is utilized to capture mAb. Human and cynomolgus monkey PD1-ECD proteins which contain a C-terminal 8× histidine tag are expressed in CHO cells and purified by nickel charged IMAC followed by size exclusion.

Binding is evaluated using multiple analytical cycles. Each cycle is performed at 25° C. at a flow rate of 10 µl/minute for mAb capture and 30 µl/minute for ligand association and dissociation. Each cycle consists of the following steps: injection of mAb at 2 µg/ml for 60 s contact time targeting a capture level of approximately 220RUs on flow cell 2, injection of 150 seconds of human or cynomolgus PD1-ECD-his (concentration range of 400 nM to 1.6 nM by four fold serial dilution) followed by 600 second dissociation phase, and regeneration using 10 mM glycine hydrochloride, pH 1.5 over a 30 second contact time. Association (i.e., Kon) and dissociation rates (i.e., Koff) for each cycle are evaluated using standard double referencing and fit to "1:1 (Langmuir) binding" model in the Biacore 8K evaluation in parallel kinetics batch mode. The affinity ($K_D$) is calculated from the binding kinetics according to the relationship $K_D$=Koff/Kon.

In subsequent experiments, Biacore was used to measure the binding kinetics for Antibody 1 to human and cynomolgus monkey PD1-extracellular domain (ECD)-His via surface plasmon resonance (SPR) at 37° C. by BIAcore® T200. For analyses at 37° C., binding is evaluated using multiple analytical cycles. Each cycle is performed at 37° C. at a flow rate of 10 µl/minute for mAb capture and 100 µl/minute for ligand association and dissociation. Each cycle consists of the following steps: injection of mAb at 2.5 µg/ml targeting a capture level of approximately 220RUs on flow cell 2, injection of 180 seconds of human or cynomolgus PD1-ECD-his (concentration range of 1000 nM to 1.6 nM by 2-fold serial dilution) followed by 600 second dissociation phase, and regeneration using 10 mM glycine hydrochloride, pH 1.5 over a 30 second contact time. Kon, Koff, and $K_D$ are calculated essentially as described above. Affinity data is reported as average and standard deviations determined from triplicate measurements in three independent experiments (mean±SD, n=9).

In experiments performed essentially as described above, Antibody 1 binds to human and cynomolgus monkey PD1-ECD-his as determined by Biacore at 25° C. (n=1) and at 37° C. (n=9) and as illustrated in Table 2.

TABLE 2

Kinetics and Affinity of Antibody 1 binding to PD-1 ECD

| | PD-1 ECD species | $K_{on}$ (1/MS) | $K_{off}$ (1/s) | KD (nM) |
|---|---|---|---|---|
| 25° C. | Human | 1.7E+05 | 1.7E−04 | 1.0 |
| | Cynomolgus | 2.4E+05 | 1.1E−03 | 4.7 |
| 37° C. | Human | 3.07 ± 0.16 × $10^5$ | 7.01 ± 0.92 × $10^{-4}$ | 2.29 ± 0.36 |
| | Cynomolgus | 5.19 ± 0.52 × $10^5$ | 4.89 ± 0.10 × $10^{-3}$ | 9.51 ± 0.85 |

As shown in Table 2, Antibody 1 binds both human and cynomolgus monkey PD-1 ECD with nanomolar affinity and demonstrates similar binding kinetics on both human and cynomolgus monkey PD-1 ECD.

EXAMPLE 4: ANTIBODY 1 DOES NOT BLOCK BINDING OF PD-1 TO PD-L1 OR PD-L2

The ability of an antibody of the present invention to block PD-1 binding to PD-L1 and PD-L2 can be determined as follows. Briefly described, human PD-1 expressing stable cells are generated by transfecting human PD-1 plasmid DNA into CHO-k1 cells (Lonza) using an electroporation system (Gene Pulser Xcell; BioRad) according to established protocols. Stable cells are selected from single isolated cells using 500 µg/mL G418 (Thermo Scientific) in culture medium. Test PD-1 antibodies at 200 µg/mL or starting at 100 µg/mL followed by 12-fold 7 point antibody titration in FACS buffer are incubated at 4° C. for 30 minutes. The cells are washed twice with FACS buffer. The cells are resuspended in 50 µl of FACS buffer with 20 µg/mL biotinylated human PD-L1 (Acros, #PD-1-H82F3) or PD-L2 (Abcam, ab198764) and incubated at 4° C. for 30 minutes. The cells are washed twice with FACS buffer, and resuspended in 100 microliters of FACS buffer with Streptavidin-APC (BD Biocsienses, #554067) at 1:200 dilution in FACS buffer, and incubated at 4° C. for 30 minutes. After washing twice in FACS buffer, live/dead cell staining is performed using SytoxBlue (Invitrogen, #S34857) per manufacturer's protocol. Cells are processed on Fortessa, Fortessa Fx or LSRII flow cytometry instrument. Flow cytometry data is analyzed using FlowJo software. Mean Fluorescence intensity (MFI) values are used to calculate relative $IC_{50}$ based on 4-parameter logistic regression.

In experiments performed essentially as described above, Antibody 1 and the isotype control antibody did not block PD-L1 nor PD-L2 binding, the $IC_{50}$ of the positive control antibody, a PD-1 specific antagonist antibody (homolog to nivolumab), was 0.22+/−0.02 µg/mL for PD-L1 and 0.42+/−0.12 µg/mL for PD-L2. These data demonstrate that Antibody 1 does not block PD-1 binding to PD-L1 or PD-L2.

EXAMPLE 5: ANTIBODY 1 INHIBITS T CELL RECEPTOR ACTIVATION INDUCED NFAT SIGNALING

NFAT (Nuclear factor of activated T cells) is a transcription factor that plays an important role in mediating T cell receptor activation to immune response by modulating expression of genes encoding inflammatory cytokines, e.g., TNF, IL-2 as well as several cell surface receptors. The ability of the antibodies disclosed herein to inhibit T cell receptor activation induced NFAT signaling can be measured as follows.

Briefly described, Jurkat T cell transfected with both NFAT luciferase reporter and human PD-1 (Promega) are activated with human CD3 antibody and THP-1 cells (ATCC). THP-1 cells (40,000 cells/well) are plated in 100 μl to a white 96-well plate (Corning, #3917). Two μg/mL of anti-human CD3 antibody (OKT3) (eBioscience, #16-0037) and treatment antibodies (Antibody 1 or isotype control antibody) at final concentration of 20 μg/mL or a five-fold 7-point antibody titration starting at 10 μg/mL are added onto the THP-1 cells. The cell and antibody mixtures are incubated at 37° C., 5% $CO_2$ for 30 minutes. NFAT-luciferase Jurkat reporter cells expressing PD-1 (50,000 cells/ well) are added onto the THP-1 cells, CD3 antibody and treatment antibody mixtures on 96-well plates, and incubated at 37° C., 5% $CO_2$ for 5 hours. At the end of the incubation, the plates are brought to room temperature for 10 minutes. Eighty (80) microliters of BioGlo reagent (Promega, #G7940) are added to the wells, and incubated for 10 minutes at room temperature. Luminescence is ready by LMaxII384 (Molecular Devices) or Envision 2105 (Perkin Elmer).

In experiments performed essentially as described above, Antibody 1 and isotype control antibody inhibited human PD-1 NFAT-luciferase reporter cell activity with an average $IC_{50}$ from four independent experiments of 75.2+/−37.6 ng/mL whereas isotype control antibody did not significantly inhibit NFAT signaling. These data demonstrate that Antibody 1 is able to inhibit T cell receptor activation induced NFAT signaling.

EXAMPLE 6: ANTIBODY 1 INHIBITS HUMAN PRIMARY T CELL PROLIFERATION

The ability of the antibodies disclosed herein to inhibit T cell proliferation induced by T cell receptor activation can be measured as follows. Briefly described, human peripheral blood mononuclear cells (PBMCs) are isolated from healthy human Trima LRS (San Diego Blood Bank; San Diego, Calif.) using Ficoll density gradient centrifugation method by overlaying 35 mL diluted blood (tenfold dilution in PBS without calcium or magnesium onto 15 mL 37° C. Ficoll (Ficoll-Paque Plus, GE Healthcare; Ser. No. 17/144,002) in 50 mL conical tubes. Tubes are centrifuged at room temperature for 30 minutes at 900×G. The cell interface is transferred to a new 50 mL conical tube. The final volume is adjusted to 50 mL with room temperature PBS (without calcium or magnesium). After washing twice in PBS, the cells are resuspended in complete CTS media (Gibco, #A1048501; #A10484-02).

Isolated human PBMCs are labelled with CFSE (Biolegend, cat. #79898). PBMCs are washed three times in serum free RPMI. CFSE labelling is carried out in serum free media in the presence of 1 μM CFSE at 37° C. with 5% $CO_2$ for 20 minutes The CFSE is quenched with complete CTS media followed by a wash step.

The CFSE labelled PBMCs (150,000 cell/well) are added to each 96-well round bottom well containing Antibody 1 or isotype control antibody. The cells are stimulated with 4 ng/mL superantigen (Staphylococcal Enterotoxin, SEB) (Toxin Technologies BT2021MG) for 72 hours at 37° C. with 5% $CO_2$.

Post-incubation plates are washed with FACS buffer (Miltenyi Biotec; #130-091-221), incubated with human Fc blocking reagent (Miltenyi Biotec, #130-059-901) for 10 minutes followed by staining with labelled antibodies against CD4 (Biolegend, #317426) and PD-1 (eBioscience, #17-2799-42) for 30 minutes on ice. After washing in FACS buffer, live/dead cell staining is performed using SytoxBlue (Invitrogen, #S34857) per manufacturer's protocol. Cells are processed on Fortessa X20 flow cytometry instrument in the presence of CountBright Beads (Invitrogen, #C36950) to quantitate the cell number. Flow cytometry data is analyzed using FlowJo software. Absolute dividing CD4 positive cell count is calculated using CFSE staining and CountBright beads.

In experiments performed essentially as described above, Antibody 1 was able to inhibit human primary T cell proliferation with an average $IC_{50}$ of 175+/−128 ng/mL for eight different donors, whereas isotype control antibody did not inhibit primary T cell proliferation. These data demonstrate that Antibody 1 is able to inhibit T cell proliferation in vitro.

EXAMPLE 7: IN VITRO CYTOKINE RELEASE STUDIES

The aim of this study is to test whether Antibody 1 induces cytokine release from unstimulated human PBMCs.

Briefly described, freshly isolated PBMCs from healthy subjects are incubated with plate bound Antibody 1, or control antibodies for 24 hours, over a titration range from 0.5 μs to 1.5 μg. The positive controls are a commercially available anti-human CD3c antibody, OKT3, and a homolog of CD28-specific superagonist therapeutic antibody, TGN1412. Both antibodies are known to cause cytokine release syndrome, a form of systemic inflammatory response syndrome that can be life-threatening. The negative control is a human IgG1 wild type (WT) isotype control antibody. Using a commercially available multiplex assay based on the Mesoscale platform, five cytokines including, IFN-γ, IL-2, IL-6, IL-10, and TNF-α are measured in cell culture supernatants.

In experiments performed essentially as described above, incubation of human PBMCs with Antibody 1 did not result in significant levels of cytokine release for IFN-γ, IL-2, IL-6, IL-10, and TNF-α at the concentrations of 0.5, 1, or 1.5 μg/well. In contrast, incubation of PBMCs with anti-CD3c and TGN1412 positive control antibodies at 1 μg per well resulted in robust production of IL-2, IFN-γ, IL-10 and TNF-α in most donors.

EXAMPLE 8: MOUSE GRAFT-VERSUS-HOST DISEASE (GVHD) IN VIVO MODEL

Humanized mouse models of xenogeneic-GvHD based upon immunodeficient strains injected with human PBMCs ("Hu-PBMC mice") are important tools to study human immune function in vivo. The ability of antibodies disclosed herein to protect mice from GvHD is evaluated in Hu-PBMC mice model.

Briefly described, female NSG mice (NOD.Cg-Prkdcscid Il2rgtm1Wjl/SzJ, JAX Labs, Stock #05557) are housed 3 per cage at 72° C. under a 12 hour light:dark cycle and allowed food and water ad libitum (n=78). Human PBMCs are isolated from LRS tubes obtained from two donors (San Diego Blood Bank) using SepMate 50 Ficoll preparation tubes according to the manufacturer's instructions (STEM-CELL Technologies, Vancouver, BC). Freshly isolated PBMCs are suspended in PBS at $1.2 \times 10^8$ cells/mL and mice are engrafted with 100 μL PBMCs suspension intravenously on day 0 ($1.2 \times 10^7$/mouse); 36 mice receive PBMCs from Donor 1, 36 from Donor 2, and 6 mice remained non-engrafted controls. Identical protocols are subsequently followed for each donor. On day 1, mice are divided into four weight matched groups/donor and dosed with isotype control or Antibody 1 at 0.1, 1.0 or 10.0 mg/kg subcutaneously (200 μL/mouse). Dosing continues twice weekly for the remainder of the experiment. Health checks and body weight measurements are performed routinely. Mice that lose 20% of their starting weight or are in obvious distress are euthanized. When the majority of isotype control mice are in need of euthanasia due to the progression of disease, all mice are sacrificed. For all euthanized mice, blood is collected by cardiac puncture under isoflurane anesthesia into EDTA tubes for FACS analysis and clarified by centrifugation for plasma analyses. Body weight and clinical observations: Mice are weighed in a BSL2 hood and assessed for clinical signs of distress 2-3 times/week. Clinical signs common to this model are scruffy hair, hunched body, wasting, and labored breathing or movement. Body weight change is calculated as a percentage of their baseline weight: (Day (x) weight/Day 0 weight)*100.

Plasma Analyses:

Blood from the cardiac puncture is collected into EDTA coated tubes, clarified by centrifugation, and the resultant plasma is stored at −80° C. for future processing. Plasma cytokines are measured using the Mesoscale Discovery Human Th1/Th2 10-Vplex (Rockville, Md.) according to the manufacturer's instructions.

Statistics:

Data are graphed and statistics are calculated using Prism Software (GraphPad, San Diego, Calif.). Differences in weights between groups are determined by 2-way RM-ANOVA with Tukey's post hoc test. Differences in terminal plasma cytokine levels are determined by 1-way ANOVA with Tukey's post hoc test. Differences between test groups are considered significant if $p<0.05$.

In experiments performed essentially as described above, engraftment of human PBMCs from Donor 1 or Donor 2 elicited GvHD as evidenced by marked wasting in NSG mice. Disease progression was more rapid in mice engrafted with Donor 2 PBMCs compared to Donor 1 with study terminations due to significant weight loss on days 26 and 40, respectively. Treatments with Antibody 1 significantly attenuated disease progression as measured by a reduction in weight loss in mice engrafted with either donor. Additionally, Antibody 1 inhibited the pronounced increase in plasma human Th1 (IFN-γ) and Th2 (IL-13) cytokines associated with disease progression. Therefore, Antibody 1 significantly reduces disease progression in a humanized GvHD model.

EXAMPLE 9: HPD-1 K1 TO BM12 CHRONIC GVHD MOUSE MODEL OF LUPUS NEPHRITIS

A chronic GvHD (cGvHD) characterized by development of auto-antibodies and pathology similar to human lupus nephritis can be induced in Bm12 mice by injecting splenocytes from donor mice expressing human PD-1 on a C57BL/6 background. In the study described in this Example 9, splenocytes from hPD-1 KI mice (C57BL/6-Pdcd1<tm1606.1) are injected into B6(C)-H2-Ablbm12/KhEgJ (Bm12) mice. Subsequently, the host mice develop a slowly progressive SLE-like disease characterized by development of autoantibodies against dsDNA and immune-complex deposition in the kidneys. Thus, the activities of a PD-1 agonist antibody may be evaluated in this lupus nephritis model as follows.

Briefly described, male human PD-1 knock-in mice (Taconic Laboratories) are 9 weeks of age upon arrival and male Bm12 mice (Jackson Laboratories) are 11 weeks of age upon arrival. All mice are housed 4 per cage and allowed to acclimate for 1 week prior to study start. The mice are fed with Teklad Global Rodent Diet 2014 (Harlan) and water ad libitum. The mice are housed in 12-hour light/dark cycle with ambient temperature set at 68-79° F. Four days before the study start, the mice are randomly sorted based on body weight and $75_1 1.1$ of whole blood are collected via tail nick. Serum is separated from the whole blood by centrifuging at 10,000 rpm for 5 minutes and used to quantitate anti-dsDNA titers. The mice are then distributed into the following treatment groups: (1) 10.0 mg/kg hIgG1 isotype control, (2) 1.0 mg/kg Antibody 1, (3) 10.0 mg/kg Antibody 1. The mice are dosed with human IgG1 isotype control or Antibody 1 subcutaneously twice per week starting on Day 0. Serum samples are collected via tail nick from the mice every 2 weeks until study termination 42 days after treatment initiation.

Serum anti-dsDNA levels are measured by a custom ELISA. Plates (96 well) are coated overnight at 4° C. with 10 μg/ml calf thymus DNA (R&D Systems). Following washes with PBS-Tween (0.05%), 2 μl of sample is added (1:100 dilution) and serially diluted 1:3. After a 2 hour incubation at RT, the plates are washed and goat anti-mouse IgG (Jackson ImmunoResearch) is added at a 1:2000 dilution for 90 minutes. The plates are washed and Ultra-TMB (ThermoSci Pierce) is added for 15 minutes and the reaction is stopped with 1N H2S04. The ODs are read at 450 nm wavelength and $EC_{50}$ values are calculated.

In experiments performed essentially as described above in the Example 9, autoantibodies against double-stranded DNA (anti-dsDNA) titers were reduced with Antibody 1 treatment in a dose-dependent manner during the course of the study. At doses of 1 mg/kg and 10 mg/kg of Antibody 1, reductions in anti-dsDNA levels were statistically significant from the human IgG1 isotype control group at days 28 and 42. Anti-dsDNA AUCs were also dose-dependently reduced by Antibody 1. Antibody 1 at 10 mg/kg was able to reduce anti-dsDNA AUC significantly from the human IgG1 isotype control. Therefore, Antibody 1 can significantly reduce disease progression in a cGvHD model of lupus.

```
                Amino Acid and Nucleotide Sequences

Heavy Chain of Antibody 1 (SEQ ID NO: 1)
QVQLVQSGAEVKKPGASVKVSCKVSGYSLSKYDMSWVRQAPGKGLEWMGIIYT
SGYTDYAQKFQGRVTMTEDTSTDTAYMELSSLRSEDTAVYYCATGNPYYTNGF
NSWGQGTLVTVSSASTKGPSVFPLAPSSKSTSGGTAALGCLVKDYFPEPVTVSWN
SGALTSGVHTFPAVLQSSGLYSLSSVVTVPSSSLGTQTYICNVNHKPSNTKVDKK
VEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCK
VSNKALPAPIEKTISKAKGQPREPQVYTLPPSRDELTKNQVSLTCLVKGFYPSDIA
VEWESNGQPENNYKTTPPVLDSDGSFFLYSKLTVDKSRWQQGNVFSCSVMHEAL
HNHYTQKSLSLSPGK
```

| Amino Acid and Nucleotide Sequences |
|---|
| Light Chain of Antibody 1 (SEQ ID NO: 2)<br>DIQMTQSPSSLSASVGDRVTITCQASQSPNNLLAWYQQKPGKAPKLLIYGASDLP<br>SGVPSRFSGSGSGTDFTLTISSLQPEDFATYYCQNNYYVGPVSYAFGGGTKVEIKR<br>TVAAPSVFIFPPSDEQLKSGTASVVCLLNNFYPREAKVQWKVDNALQSGNSQESV<br>TEQDSKDSTYSLSSTLTLSKADYEKHKVYACEVTHQGLSSPVTKSFNRGEC<br><br>Heavy Chain Variable Region of Antibody 1 (SEQ ID NO: 3)<br>QVQLVQSGAEVKKPGASVKVSCKVSGYSLSKYDMSWVRQAPGKGLEWMGIIYT<br>SGYTDYAQKFQGRVTMTEDTSTDTAYMELSSLRSEDTAVYYCATGNPYYTNGF<br>NSWGQGTLVTVSS<br><br>Light Chain Variable Region of Antibody 1 (SEQ ID NO: 4)<br>DIQMTQSPSSLSASVGDRVTITCQASQSPNNLLAWYQQKPGKAPKLLIYGASDLP<br>SGVPSRFSGSGSGTDFTLTISSLQPEDFATYYCQNNYYVGPVSYAFGGGTKVEIK<br><br>HCDR1 of Antibody 1 (SEQ ID NO: 5)<br>KVSGYSLSKYDMS<br><br>HCDR2 of Antibody 1 (SEQ ID NO: 6)<br>IIYTSGYTDYAQKFQG<br><br>HCDR3 of Antibody 1 (SEQ ID NO: 7)<br>ATGNPYYTNGFNS<br><br>LCDR1 of Antibody 1 (SEQ ID NO: 8)<br>QASQSPNNLLA<br><br>LCDR2 of Antibody 1 (SEQ ID NO: 9)<br>YGASDLPS<br><br>LCDR3 of Antibody 1 (SEQ ID NO: 10)<br>QNNYYVGPVSYA<br><br>DNA Encoding the Heavy Chain of Antibody 1 (SEQ ID NO: 11)<br>caagtgcagttggtgcagtcggggggcagaagtgaaaaagcccggcgcttcggtgaaagtgtcctgcaaagtgtccggctattct<br>ttgtccaaatacgacatgtcatgggtcagacaggctcccggaaagggtctggagtggatggggattatctatacatccggctaca<br>ccgattacgcccaaaagttccaggggagagtcaccatgactgaggatacgtccaccgacaccgcctcatggaactgtccagc<br>ctgcggtccgaggacactgcggtgtactactgcgcgaccggaaaccatactacaccaatggattcaatagctggggacaggg<br>tactcttgtgacggtgtccagcgcctccaccaagggcccatcggtcttccctgctagcacactcctccaagagcacctctgggggc<br>acagcggccctgggctgcctggtcaaggactacttccccgaaccggtgacggtgtcgtggaactcaggcgccctgaccagcg<br>gcgtgcacaccttcccggctgtcctacagtcctcaggactctactccctcagcagcgtggtgaccgtgccctccagcagcttggg<br>cacccagacctacatctgcaacgtgaatcacaagcccagcaacaccaaggtggacaagaaagttgagcccaaatcttgtgaca<br>aaactcacacatgccaccgtgcccagcacctgaactcctgggggggaccgtcagtcttcctcttcccccccaaaacccaaggaca<br>ccctcatgatctccccggacccctgaggtcacatgcgtggtggtggacgtgagccacgaagacctgaggtcaagttcaactggt<br>acgtggacggcgtggaggtgcataatgccaagacaaagccgcgggaggagcagtacaacagcacgtaccgtgtggtcagcg<br>tcctcaccgtcctgcaccaggactggctgaatggcaaggagtacaagtgcaaggtctccaacaaagcccctcccagccccatc<br>gagaaaaccatctccaaagccaaagggcagccccgagaaccacaggtgtacaccctgcccccatcccgggacgagctgacc<br>aagaaccaggtcagcctgacctgcctggtcaaaggcttctataccagcgacatcgccgtggagtgggagagcaatgggcagc<br>cggagaacaactacaagaccacgcccccgtgctggactccgacggctccttcttcctctatagcaagctcaccgtggacaaga<br>gcaggtggcagcaggggaacgtcttctcatgctccgtgatgcatgaggctctgcacaaccactacacgcagaagagcctctccc<br>tgtctccgggtaaa<br><br>DNA Encoding the Light Chain of Antibody 1 (SEQ ID NO: 12)<br>gacatccagatgacccagtctccatcctcctgtctgcatctgtgggagacagagtcaccatcacttgccaggccagtcagagcc<br>ctaataacctcctggcctggtatcagcagaaaccagggaaagcccctaagctcctgatctatggtgcatccgatctgccatctgg<br>ggtcccatcaaggttcagtggcagtggatctgggacagatttcactctcaccatcagcagtctgcaacctgaagattttgcaact<br>tactactgtcagaacaattattatgtgggaccagtgagctatgctttcggcggagggaccaaggtggagatcaagcggaccgtgg<br>ctgccaccatctgtcttcatcttcccgccatctgatgagcagttgaaatctggaactgcctctgttgtgtgcctgctgaataactt<br>ctatcccagagaggccaaagtacagtggaaggtggataacgccctccaatcgggtaactcccaggagagtgtcacagagcaggac<br>agcaaggacagcacctacagcctcagcagcaccctgacgctgagcaaagcagactacgagaaacacaaagtctacgcctgcgaa<br>gtcacccatcagggcctgagctcgcccgtcacaaagagcttcaacaggggagagtgc<br><br>Amino acid sequence of human PD-1 (SEQ ID NO: 13)<br>MQIPQAPWPVVWAVLQLGWRPGWFLDSPDRPWNPPTFSPALLVVTEGDNATFT<br>CSFSNTSESFVLNWYRMSPSNQTDKLAAFPEDRSQPGQDCRFRVTQLPNGRDFH<br>MSVVRARRNDSGTYLCGAISLAPKAQIKESLRAELRVTERRAEVPTARPSPSPRPA<br>GQFQTLVVGVVGGLLGSLVLLVWVLAVICSRAARGTIGARRTGQPLKEDPSAVP<br>VFSVDYGELDFQWREKTPEPPVPCVPEQTEYATIVFPSGMGTSSPARRGSADGPR<br>SAQPLRPEDGHCSWPL<br><br>Amino acid sequence of human PD-1 ECD (SEQ ID NO: 14)<br>LDSPDRPWNPPTFSPALLVVTEGDNATFTCSFSNTSESFVLNWYRMSPSNQTDKL<br>AAFPEDRSQPGQDCRERVTQLPNGRDEHMSVVRARRNDSGTYLCGAISLAPKAQI<br>KESLRAELRVTERRAEVPTARPSPSPRPAGQFQ |

Amino Acid and Nucleotide Sequences

Amino acid sequence of cynomolgus monkey PD-1 (SEQ ID NO: 15)
MQIPQAPWPVVWAVLQLGWRPGWELESPDRPWNAPTFSPALLLVTEGDNATFT
CSFSNASESFVLNWYRMSPSNQTDKLAAFPEDRSQPGQDCRFRVTRLPNGRDFH
MSVVRARRNDSGTYLCGAISLAPKAQIKESLRAELRVTERRAEVPTARPSPSPRPA
GQFQALVVGVVGGLLGSLVLLVWVLAVICSRAAQGTIEARRTGQPLKEDPSAVP
VFSVDYGELDFQWREKTPEPPAPCVPEQTEYATIVFPSGLGTSSPARRGS ADGPRS
PRPLRPEDGHCSWPL Amino acid sequence of cynomolgus monkey PD-1 ECD (SEQ ID NO: 16)
LESPDRPWNAPTFSPALLLVTEGDNATFTCSFSNASESFVLNWYRMSPSNQTDKL
AAFPEDRSQPGQDCRFRVTRLPNGRDFHMSVVRARRNDSGTYLCGAISLAPKAQI
KESLRAELRVTERRAEVPTAHPSPSPRPAGQFQ Amino acid sequence of human IgG1 (SEQ ID NO: 17):
ASTKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKKVEP
KSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGK
EYKCKVSNKALPAPIEKTISKAKGQPREPQVYTLPPSRDELTKNQVSLTC
LVKGFYPSDIAVEWESNGQPENNYKTTPPVLDSDGSFFLYSKLTVDKSRW
QQGNVFSCSVMHEALHNHYTQKSLSLSPGK Amino acid sequences of wild-type human kappa (SEQ ID NO: 18)
RTVAAPSVFIFPPSDEQLKSGTASVVCLLNNFYPREAKVQWKVDNALQSG
NSQESVTEQDSKDSTYSLSSTLTLSKADYEKHKVYACEVTHQGLSSPVTK
SFNRGEC Amino acid sequence of wild-type human lambda (SEQ ID NO: 19)
GQPKANPTVTLFPPSSEELQANKATLVCLISDFYPGAVTVAWKADGSPVK
AGVETTKPSKQSNNKYAASSYLSLTPEQWKSHRSYSCQVTHEGSTVEKT
VAPTECS

We claim:

1. An antibody that binds human PD-1, comprising: 1) a heavy chain variable region (HCVR); and 2) a light chain variable region (LCVR), wherein the HCVR comprises a HCDR1, HCDR2, and HCDR3, and the LCVR comprises a LCDR1, LCDR2, and LCDR3, wherein the amino acid sequence of the HCDR1 is SEQ ID NO:5, the amino acid sequence of the HCDR2 is SEQ ID NO:6, and the amino acid sequence of the HCDR3 is SEQ ID NO:7, the amino acid sequence of the LCDR1 is SEQ ID NO:8, the amino acid sequence of the LCDR2 is SEQ ID NO:9, and the amino acid sequence of the LCDR3 is SEQ ID NO:10, and wherein the antibody is an IgG1.

2. The antibody of claim 1, wherein the amino acid sequence of the HCVR is SEQ ID NO:3 and the amino acid sequence of the LCVR is SEQ ID NO:4.

3. The antibody of claim 2 comprising: 1) a HC; and 2) a LC, wherein the amino acid sequence of the HC is SEQ ID NO:1, and the amino acid sequence of the LC is SEQ ID NO:2.

4. The antibody of claim 3 comprising two HCs and two LCs, wherein the amino acid sequence of each of the HCs is SEQ ID NO:1, and the amino acid sequence of each of the LCs is SEQ ID NO:2.

5. The antibody of claim 1, wherein the antibody is an agonist of human PD-1 as determined in an in vivo model of an autoimmune disorder or transplant rejection.

6. The antibody of claim 5 wherein the in vivo model is a model for GVHD, solid organ transplantation rejection, vasculitis, SLE, T1DM, MS, GCA, PsO, PsA, RA, IBD, UC, AS, SjS, autoimmune hepatitis, or scleroderma.

7. The antibody of claim 5 wherein the in vivo model is a mouse model for GVHD and/or lupus nephritis.

8. A pharmaceutical composition comprising the antibody of claim 1, and one or more pharmaceutically acceptable carriers, diluents, or excipients.

9. A method of treating an autoimmune disease comprising administering to a patient in need thereof, an effective amount of the antibody of claim 1.

10. The method of claim 9, wherein the autoimmune disease is GVHD, solid organ transplantation rejection, vasculitis, SLE, T1DM, MS, GCA, PsO, PsA, RA, IBD, UC, AS, SjS, autoimmune hepatitis, scleroderma, celiac disease, Addison's disease, Hashimoto's disease, Graves' disease, atrophic gastritis/pernicious anemia, acquired hypogonadism/infertility, hypoparathyroidism, Coombs positive-hemolytic anemia, chronic allergic diseases (such as asthma, hay fever, or allergic rhinitis), Crohn's disease, male or female infertility, Behcet's, Wegener's granulomatosis, myocarditis, myositis, PMR, spontaneous abortion, vitiligo, atherosclerosis, autoimmune pancreatitis, bullous pemphigoid, chronic viral infections, or myasthenia gravis.

11. The method of claim 10, wherein the autoimmune disease is GVHD, solid organ transplantation rejection, vasculitis, SLE, T1DM, MS, GCA, PsO, PsA, RA, IBD, UC, AS, SjS, autoimmune hepatitis, or scleroderma.

12. The method of claim 10, wherein the antibody is administered in combination with another therapeutic agent effective for the treatment of an autoimmune disease.

* * * * *